United States Patent [19]

Vlassis

[11] Patent Number: 5,366,374
[45] Date of Patent: Nov. 22, 1994

[54] DENTAL IMPLANT

[76] Inventor: James M. Vlassis, 2900 S. Gessner, #1104, Houston, Tex. 77063

[21] Appl. No.: 63,532

[22] Filed: May 18, 1993

[51] Int. Cl.$^5$ .......................... A61C 3/02; A61C 8/00
[52] U.S. Cl. ............................... 433/165; 433/173
[58] Field of Search ............................ 433/165, 173

[56] References Cited

U.S. PATENT DOCUMENTS

| | | | |
|---|---|---|---|
| 1,123,730 | 1/1915 | Greenfield | 433/165 |
| 1,216,683 | 2/1917 | Greenfield | 433/165 |
| 4,365,958 | 12/1982 | Vlock | 433/225 |
| 4,744,753 | 5/1988 | Ross | 433/173 |
| 4,744,754 | 5/1988 | Ross | 433/173 |
| 4,744,755 | 5/1986 | Ross | 433/173 |
| 4,744,756 | 5/1988 | Ross | 433/173 |
| 4,820,156 | 4/1989 | Ross | 433/165 |
| 4,886,456 | 12/1989 | Ross | 433/173 |
| 5,066,230 | 11/1991 | Weissman | 433/221 |
| 5,087,201 | 2/1992 | Mondani | 433/174 |

FOREIGN PATENT DOCUMENTS 2516784  5/1983  France .............................. 433/173

OTHER PUBLICATIONS

Bertil Friberg, DDS; A New Self-Tapping Branemárk Implant: Clinical and Radiograhic Evaluation; 1992; pp. 80-84.
Franz Sutter; The New Concept of ITI Hollow-Cylinder and Hollow-Screw Implants, etc.; 1988; pp. 161-172.
Pre-Operative Guideline p. 86, vol. 3, No. 2, 1988.
John B. Brunski, PhD.; Biomaterials and Biomechanics in Dental Implant Design; 1988; pp. 85-97.
Leonard I. Linkow, DDS; Evolution of the Vent-Plant Osseointegrated Compatible Implant System; 1988; pp. 109-120.
Only Core-Vent Corporation has a Universal System Which Fits so Well Together, catalog.

*Primary Examiner*—John J. Wilson
*Attorney, Agent, or Firm*—Harris Beach & Wilcox

[57] ABSTRACT

There is disclosed an endosseous dental implant apparatus. The implant has an elongated, substantially cylindrical body, a distal hollow internal chamber and an open distal end. The distal end has a series of dentate ridges that forms a rotary cutting surface for trephining the bone. Proximally there is provided a dental handpiece adapter. At least one spiral osteogroove is disposed on the external surface of the body, extending from the distal portion generally toward the proximal portion and communicating with a recessed osteoreservoir. At least one osteovent is situated in the osteogroove, and has a leading bevelled margin to promote the ingress of bone fragments therethrough into the internal chamber. The osteoreservoir may incorporate a spiral ridge that defines a continuous spiral groove.

10 Claims, 4 Drawing Sheets

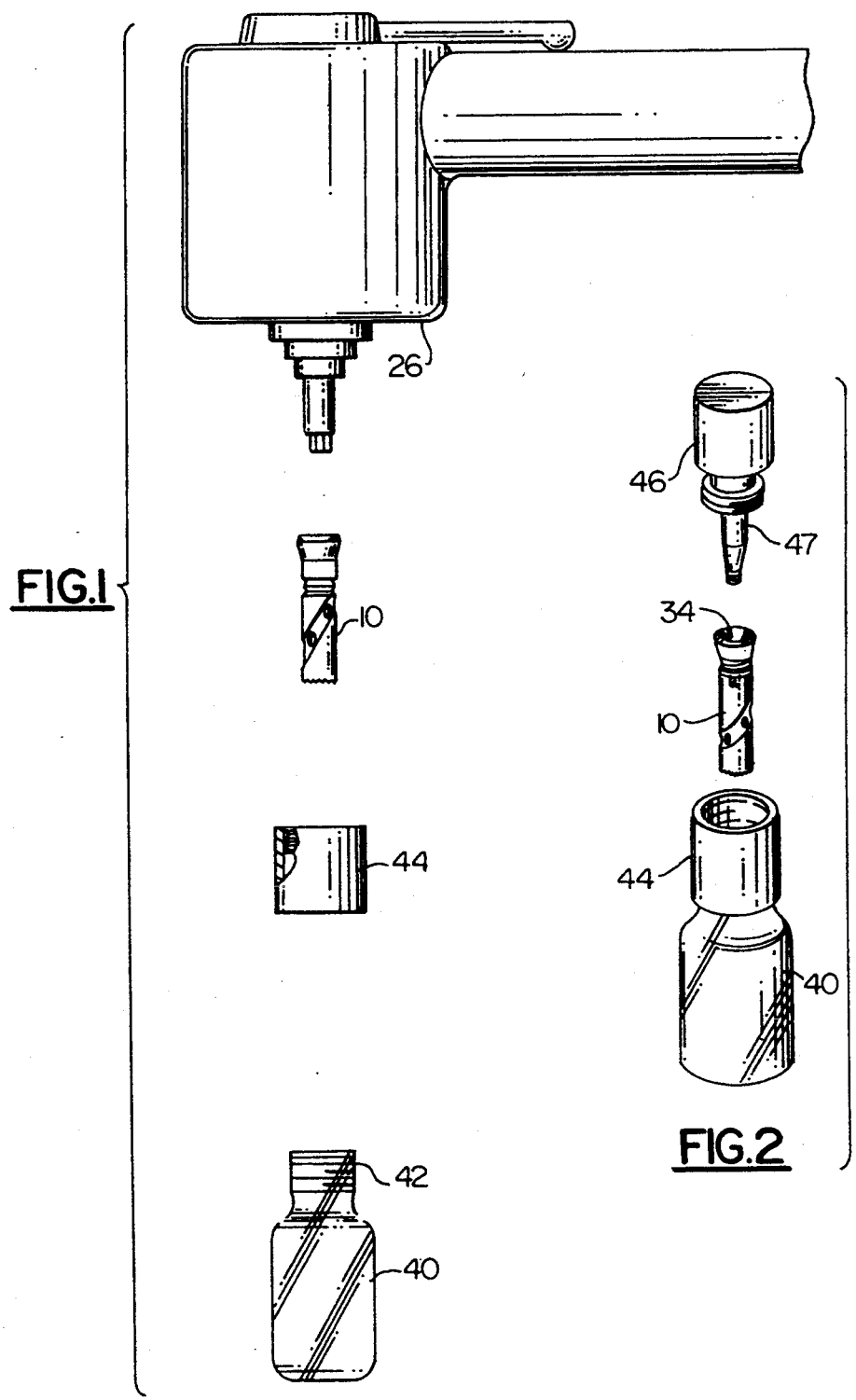

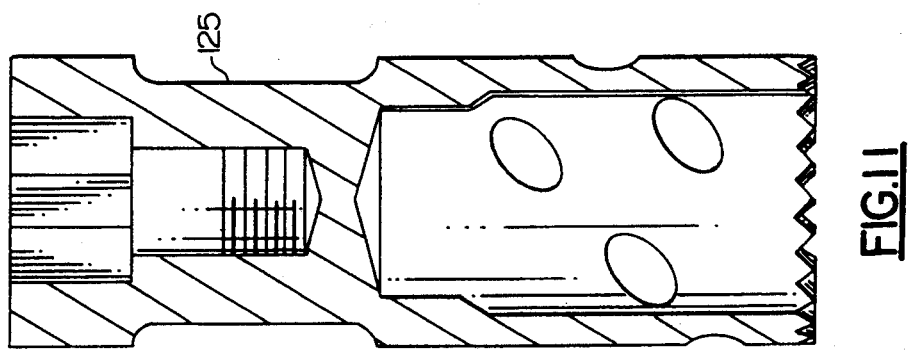
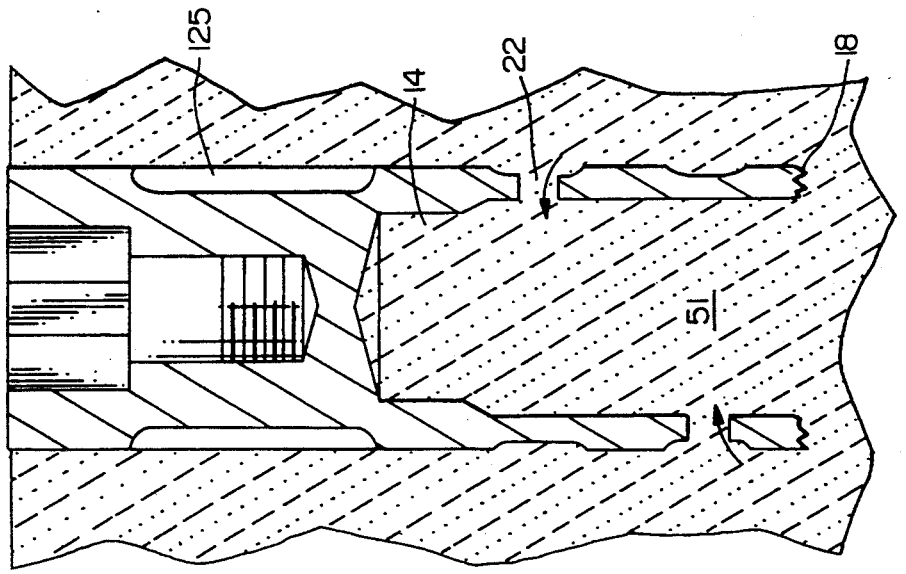

DENTAL IMPLANT

BACKGROUND OF THE INVENTION

1. Field of the Invention

This invention relates to endosseous dental implants. More particularly this invention relates to a combination osteointegrated dental implant and trephine which is placed using a one-step surgical technique.

2. Description of the Prior Art

Endosseous dental implants were first attempted in the early part of this century. Today a variety of implant designs are in widespread use in the dental arts, including hollow, self-tapping screws with sluices, hollow basket implants, Vent-Plant designs, and many others. These designs, combined with modern biomaterial science, have as their object the promotion of rapid osteointegration to stabilize the implant within the bone.

The development of these dental implants has been fraught with difficulties. With some designs an interfacial fibrous tissue reaction tends to encapsulate the implant and prevent the ingrowth of trabecular bone. It has been found that the techniques used with certain implants risk the formation of epithelial inclusions. Still other designs have relatively wide flanges that increase the surface area in apposition with bone, but have poor tolerance for misalignment and risk maxillary or palatal bone perforation. Crushing and devitalization of bone adjacent the implant during repeated instrumentation of the implant site is yet another well known problem, and is sought to be avoided by implant designs having a generally open apical architecture that lessens intraoperative hydrostatic pressure and encourages blood supply to the chamber of the implant.

Conventionally, preparation of a bed for hollow cylinder implants requires several manipulatory steps, each of which traumatizes the bone and adversely affects the healing process. After reflection of a mucoperiosteal flap, a burring step, usually conducted with a round burr, marks the implant site. The cortical bone of the alveolar crest is then pre-drilled at slow speed and under copious irrigation with chilled saline to expose the underlying cancellous bone. A trephine is then used to mill the cancellous bone and form a bed having a desired depth. The bed must be probed to confirm its depth. Only then can the implant be inserted by a hollow threaded screw or press-fitted. Variants of the above-described procedure are known, but all involve substantial insult to the bony structures that tends to impair healing and bone regeneration. Furthermore the repeated surgical instrumentation of exposed bone risks overheating of the bone, possible misalignment of the prepared site, the introduction of bacteria into the wound and the development of infection that could retard wound healing or result in failure of the implant.

SUMMARY OF THE INVENTION

It is therefore a primary object of the present invention to provide an improved dental implant capable of placement with reduced manipulation of the bone and trauma thereto.

It is another object of the present invention to provide a dental implant that has improved osteointegration properties.

It is yet another object of the present invention to provide an apparatus and a safe method for placing an implant under improved conditions of surgical sterility and with reduced risk of contamination and aspiration.

It is still another object of the present invention to provide an apparatus and method for placing a dental implant that results in rapid healing and ability of the implant to withstand masticatory and prosthetic loading.

These and other objects of the present invention are attained by an endosseous dental implant apparatus, adapted to trephine a bone for implantation therein. The implant has an elongated, substantially cylindrical body, having a distal hollow portion and an open distal end. The distal end has a series of dentate ridges that forms a rotary cutting surface for trephining the bone. There is provided a dental handpiece adapter, in order that the device can be rotated therewith about its longitudinal axis. At least one spiral osteogroove is disposed on an external surface of the body, extending from the distal portion generally toward the proximal portion for channeling a flow of bone fragments away from the cutting surface.

In accordance with one aspect of the invention a recessed osteoreservoir is disposed on the body, and communicates with the osteogroove for accumulating the channeled bone fragments. The osteoreservoir may incorporate a spiral ridge that defines a continuous spiral groove.

In accordance with another aspect of the invention the osteogroove has at least one osteovent which has a leading bevelled margin that promotes the flow of bone fragments therethrough into an internal chamber during insertion of the device, and during osteointegration.

BRIEF DESCRIPTION OF THE DRAWINGS

For a better understanding of these and other objects of the present invention, reference is made to the detailed description of the invention which is to be read in conjunction with the following drawings, wherein:

FIG. 1 is an exploded side elevation showing an apparatus in accordance with the invention in relation to dispensing equipment and a tool for manipulation;

FIG. 2 is an exploded perspective view of equipment for the sterile dispensing of the apparatus shown in FIG. 1;

FIG. 10 illustrates another alternate embodiment of the invention implanted in the bone of a patient with certain detail omitted for clarity; and FIG. 11 is a side elevation of the device shown in FIG. 10.

DESCRIPTION OF THE PREFERRED EMBODIMENT

Figure 3:
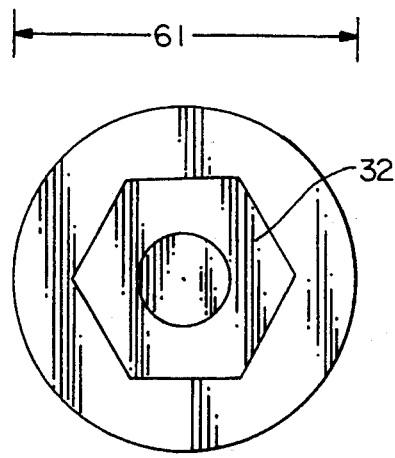
FIG. 3 is an end view along line 3—3 of FIG. 6.
Figure 4:
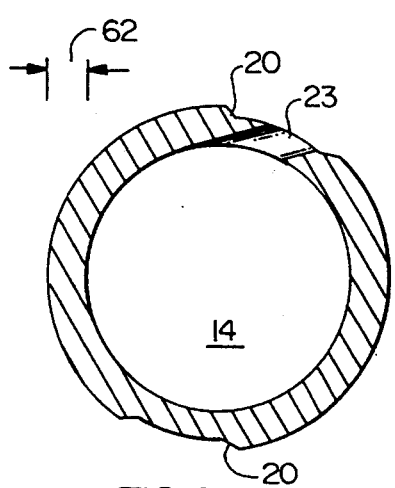
FIG. 4 is a sectional view through line 4—4 of FIG. 6.
Figure 5:
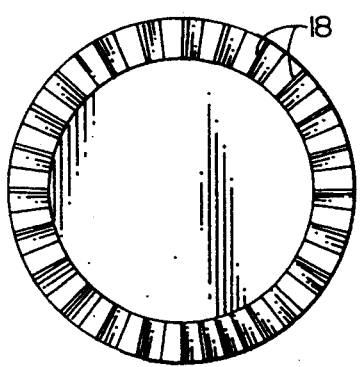
FIG. 5 is an end view along line 5—5 of FIG. 6.
Figure 6:
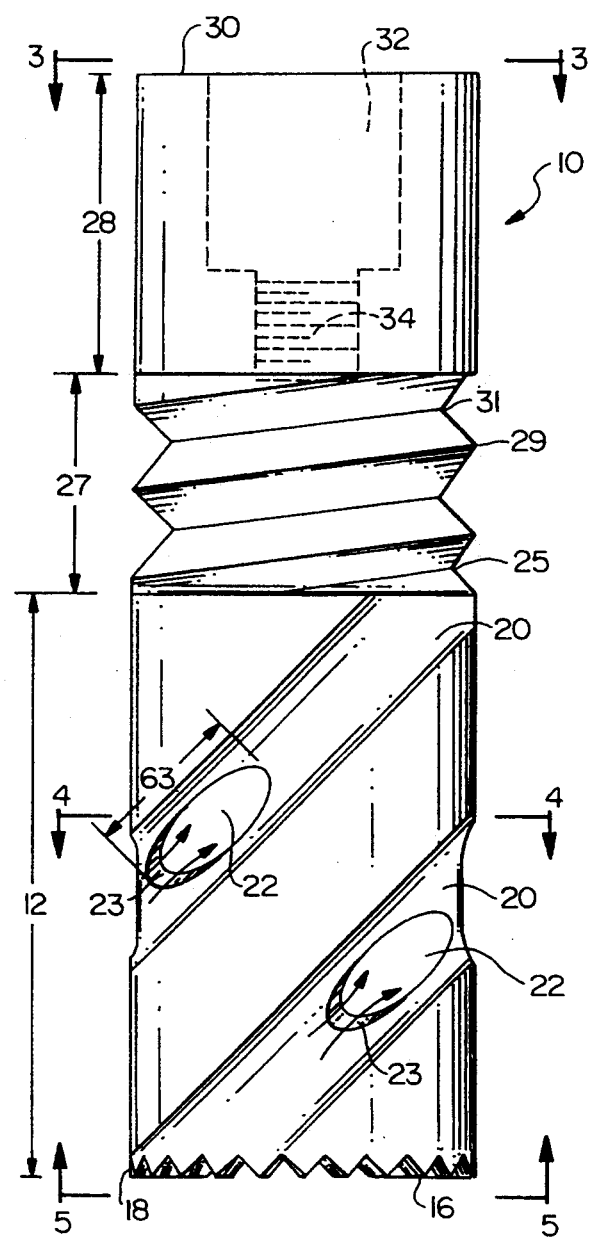
FIG. 6 is a side elevation of a preferred embodiment in accordance with the invention.

Turning now to the drawings, there is illustrated in FIGS. 1 and 3–6 a preferred embodiment of a dental implant 10 in accordance with the invention. The device comprises a combination trephine and implant that remains in position after having made a suitable kerf or cut in bone to receive a bone core therein, the inserted device remaining in place to constitute a dental implant. The implant comprises a generally cylindrical body which is fabricated of any suitable biocompatible material such as titanium or a titanium alloy, as is known to the art. The portions of that are to be in intimate contact with bone can display various surface characteristics. These portions can be titanium plasma sprayed, coated with hydroxy-apatite (HA coated), surface machined, sand blasted, or acid etched to promote osteointegration.

Implant 10 has a distal hollow portion 12 having a wall that defines an internal chamber 14, and an open distal end 16 for receiving a bone core when the device is inserted, and having thereon an annular series of sharp dentate ridges 18 that form a rotary cutting edge adapted to trephine bone into which the device is inserted. Obliquely disposed on the external surfaces of distal portion 12 are spiral osteogrooves 20, 20 which extend proximally from the distal end 16 and terminate in an osteoreservoir 25, situated on the external surface of a proximal segment of implant 10. The osteogrooves 20, 20 are provided with a plurality of osteovents 22, 22 that have two functions. First they provide access for a vascular supply to organize the bone core which is ultimately sequestered in internal chamber 14 following insertion of the implant. Secondly the osteovents 22 have beveled surfaces 23 to promote ingress of bone therethrough in the direction of the arrows in FIG. 1. during implantation. It is important that the bevel be oriented as shown. When the implant is inserted into bone while being appropriately rotated, bone fragments are generated by the action of cutting ridges 18 and are conveyed generally in an upward direction along the osteogrooves 20. Upon reaching the leading margins of osteovents 22 they are urged by external pressure into contact with the leading beveled surface 23 and thence through the osteovents 22 into chamber 14. The osteovents 22 are preferably elongated in the direction of the osteogrooves 20 in order to achieve a relatively large aperture. However they can be circular, or can be virtually any shape.

The proximal portion 28 of implant 10 is generally solid, and its proximal end 30 has a recessed hexagonal adaptor 32 adapted to attach to a conventional dental hand-piece 26 for rotation therewith about the longitudinal axis of the implant 10. The adaptor 32 communicates with a more deeply recessed internally threaded central bore 34, which affords attachment for various well known dental appliances and prostheses once the implant has been inserted and the hand-piece 26 has been removed.

Osteoreservoir 25 retains bone cuttings that result from the action of the rotary cutting surface 18 at the distal end 16 when the device is inserted. While some of the cuttings enter internal chamber 14, either directly, or via the osteovents 22 as discussed above, others are sluiced the entire extent of the osteogrooves 20 to reach osteoreservoir 25 where they accumulate and ultimately become organized into new bone. Osteoreservoir 25 is realized as a recessed segment 27 of implant 10 and is preferably provided with a spiral rib 29 that winds about the floor of the osteoreservoir and defines a continuous spiral groove 31 which communicates with the osteogrooves 20, 20. The rib 29 functionally increases the surface area of the device in external contact with bone and thereby facilitates osteointegration. As it also constitutes a system of external threads on implant 10 that engages the wall of the trephined bone cavity, a large measure of mechanical stability is added to the implant.

Dimensions of the preferred embodiment may be varied for a particular application. The dimensions and structural details of a prototype of the preferred embodiment are given in table 1, from which reference may be had to FIGS. 3-6.

TABLE 1

| Reference numeral | dimension (mm) |
|---|---|
| 61 | 4.0 |
| 62 | 1.0 |
| 63 | 1.5 |

As shown in FIG. 2, the implant 10 is packaged in a sterile vial 40 which is provided with an externally threaded neck section 42. A retainer ring 44 threadably engages neck section 42, and threadably receives cap 46. Cap 46 is provided with a threaded extension 47 that is received in central bore 34 of implant 10 to secure it within the chamber of vial 40. When the vial 40 is fully assembled implant 10 can be maintained in sterilized condition.

To use the device, a mucoperiosteal flap is prepared in the usual fashion, and the exposed cortical bone burred. Pre-drilling of the cortical bone may be performed as described above. In some applications it may be possible to even omit the pre-drilling step.

To attach the implant 10 to hand-piece 26 using sterile technique, retainer ring 44 is grasped while cap 6 is unthreaded and removed from the vial 40. The proximal section of implant 10 can then be lightly held by a suitable sterile instrument while unthreading extension 47 of cap 46 to expose adapter 32 (see FIG. 6). The distal end of hand-piece 26 is then received into adapter 32 for rotation therewith. It will be evident that this can be accomplished without the implant having been touched by the surgeon, and without breach of sterile technique.

After properly aligning the dental handpiece and the attached implant, the dental handpiece is actuated and the rotating implant brought into contact with the bone. Dentate ridges 18, 18 incisively engage the bone and develop a kerf that defines a bone core 51 which is gradually received within internal chamber 14, as best seen in FIG. 10. At the same time particulate bone cuttings are continually sluiced through osteogrooves 20, 20 into osteoreservoir 25, and also through osteovents 22, 22 so that they come into contact with bone core 51. Thus as the device is trephined into place no bone is actually removed. Instead some of the bone is simply displaced within the site, and conserved as a graft around the implant.

The above design maximizes surface area for osteointegration and withstands impact, rotational, expansive and compressive forces to which the device may be subject from time to time.

Figure 9:
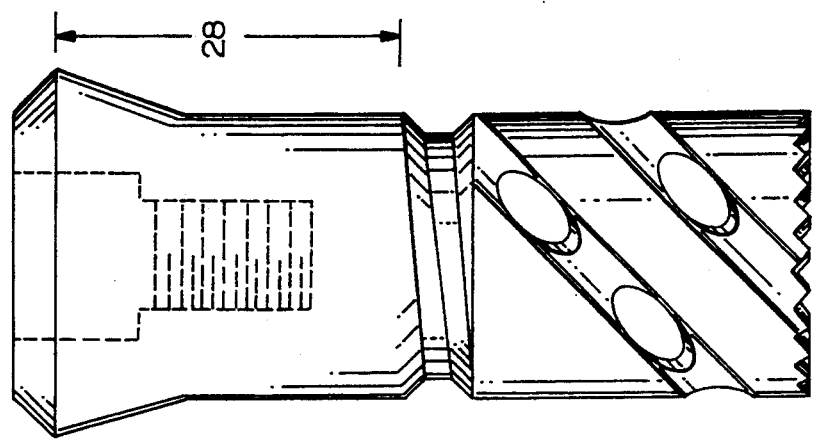
FIGS. 7–9 are side elevations of alternate embodiments of the invention.

In accordance with a first alternate embodiment of the invention, the above described device can be adapted for immediate used in extraction sockets. Reference may be had to FIG. 9, in which like components are indicated by like reference numerals. In this variant the proximal portion 28 is substantially lengthened as required by the depth of the socket. This elongated implant is driven beneath the base of the socket, and bone displaced thereby is used to graft the void resulting from extraction of a tooth. The long neck of the implant thus allows ideal opportunity for bone to regenerate around the implant in the event bone loss should occur during its life. This embodiment is suitable in nonsubmerged applications wherein the proximal end of the elongated implant is allowed to remain outside the soft tissue following its placement.

Figure 7:
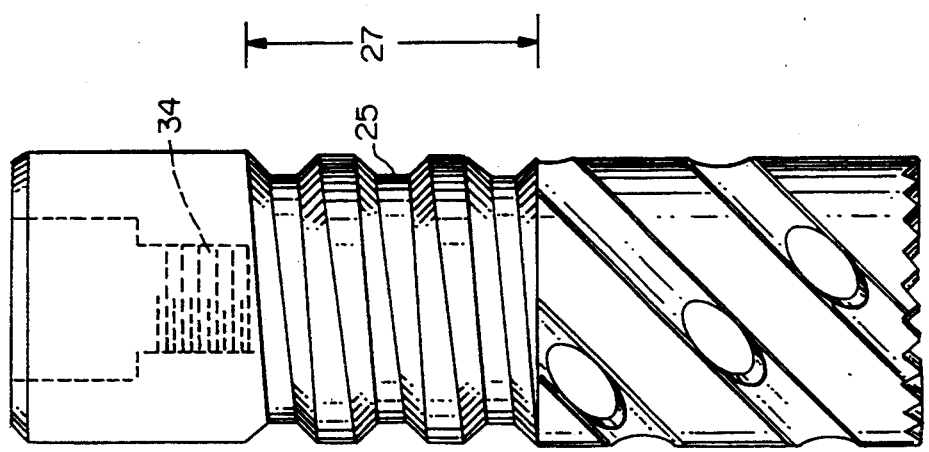

In FIG. 7 there is shown a second alternate embodiment of the invention. Segment 27, which demarcates osteoreservoir 25, is elongated to increase the capacity of the osteoreservoir, as may be desirable in certain applications.

Figure 8:
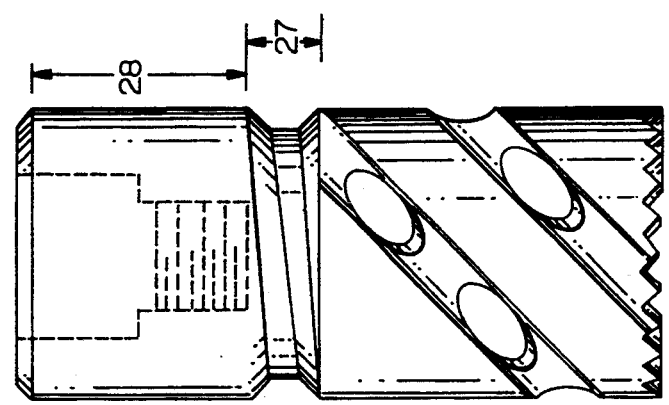

FIG. 8 illustrates a third alternate embodiment of the invention in which the segments 27 and 28 are shortened. This embodiment, while sacrificing capacity in the osteoreservoir, could be useful where there has been extensive bone loss. It minimizes the risk of penetrating the maxillary sinus or other delicate structures.

FIGS. 10 and 11 show a fourth alternate embodiment, wherein the osteoreservoir is indicated by reference numeral 125. In this variant the capacity of the osteoreservoir is still further increased by the elimination of the spiral ridge.

I thus provide an improved apparatus and method for driving a dental implant into place, in which there is minimal chance for contamination or aspiration, and the bone is only insulted once, and in one direction, thus minimizing bone trauma. As the drill or trephine teeth are only used once, they are always sharp, which further reduces the amount of trauma sustained by the bone, so that postoperative regrowth of bone and organization of the graft can readily occur.

While this invention has been explained with reference to the structure disclosed herein, it is not confined to the details set forth. For example the invention can be practiced with non-dental bone implants. This application is intended to cover any modifications and changes as may come within the scope of the following claims:

What is claimed is:

1. A permanently implantable endosseous implant apparatus, adapted to trephine a bone during implantation therein, comprising:
    an elongated, substantially cylindrical body, having a proximal portion, a distal hollow portion and an open distal end;
    cutting means disposed on said distal end of said body for trephining said bone;
    means for attachment to a handpiece for rotation therewith about an axis of said body;
    at least one spiral osteogroove, disposed on an external surface of said body, and extending from said distal portion generally toward said proximal portion for channeling a flow of bone fragments away from said cutting means;
    at least one osteovent disposed in said osteogroove for admitting bone therethrough, said osteovent having a beveled leading margin.

2. The apparatus according to claim 1, further comprising a recessed osteoreservoir that is disposed on said body, said osteoreservoir communicating with said osteogroove for accumulating said channeled bone fragments.

3. The apparatus according to claim 2, wherein said osteoreservoir comprises a spiral recess.

4. The apparatus according to claim 1, wherein said cutting means comprises a plurality of dentate ridges on said distal end.

5. An endosseous implant apparatus, adapted to trephine a bone for implantation therein, comprising:
    an elongated, substantially cylindrical body, having a distal hollow portion and an open distal end, and a proximal end;
    a series of dentate ridges disposed on said distal end of said body to form a rotary cutting surface for trephining said bone;
    a connector on said proximal end of said body adapted for attachment to a handpiece for rotation therewith about an axis of said body;
    at least one spiral osteogroove, disposed on an external surface of said body, and extending from said distal portion to a recessed osteoreservoir that is disposed on said body for channeling a flow of bone fragments from said cutting means to said osteoreservoir; and
    at least one osteovent disposed in said osteogroove for admitting bone therethrough, said osteovent having a beveled leading margin.

6. The implant apparatus according to claim 5, wherein said osteoreservoir comprises a continuous groove defined by a spiral rib that winds about said body.

7. The implant apparatus according to claim 6, wherein said proximal end of said body has a threaded bore formed therein for receiving an appliance.

8. An endosseous implant apparatus, adapted to trephine a bone for implantation therein, comprising:
    an elongated, substantially cylindrical body, having a proximal portion, a distal hollow portion and an open distal end;
    cutting means disposed on said distal end of said body for trephining said bone;
    means for attachment to a handpiece for rotation therewith about an axis of said body;
    at least one spiral osteogroove, disposed on an external surface of said body, and extending from said distal portion generally toward said proximal portion for channeling a flow of bone fragments away from said cutting means; and
    an osteoreservoir, comprising a spiral recess that is disposed on said body, said osteoreservoir communicating with said osteogroove for accumulating said channeled bone fragments.

9. A bone cutting instrument, comprising:
    an elongated, substantially cylindrical body, having a proximal portion, a distal hollow portion and an open distal end;
    cutting means disposed on said distal end of said body for trephining a bone;
    means for attachment to a handpiece for rotation therewith about an axis of said body;
    at least one spiral osteogroove, disposed on an external surface of said body, and extending from said distal portion generally toward said proximal portion for channeling a flow of bone fragments away from said cutting means; and
    at least one osteovent disposed in said osteogroove for admitting bone therethrough, said osteovent having a beveled leading margin.

10. The instrument in accordance with claim 9, further comprising:
    an osteoreservoir, comprising a spiral recess that is disposed on said body, said osteoreservoir communicating with said osteogroove for accumulating said channeled bone fragments.

* * * * *